US00PP37632P2

(12) United States Plant Patent
Hansoti

(10) Patent No.: US PP37,632 P2
(45) Date of Patent: Aug. 18, 2026

(54) ***SANSEVIERIA* PLANT NAMED 'Hansoti63'**

(50) Latin Name: *Sansevieria trifasciata*
Varietal Denomination: Hansoti63

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/349,654

(22) Filed: Oct. 3, 2025

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./382
CPC ..... A01H 6/12; A01H 5/12
See application file for complete search history.

*Primary Examiner* — Keith O. Robinson

(57) ABSTRACT

A new and distinct cultivar of *Sansevieria* plant named 'HANSOTI63' is disclosed, characterized by unique twisted, curved leaves forming a relatively flat, somewhat open spiral-form rosette that gives a vertically compressed appearance. Foliage has no variegation, only prominent cross-hatching. Plants of 'Hansoti63' present as a dark green spiral rosette with silvery green highlights due to the prominent cross hatching on a solid green background. Total mature-plant width in a 9 cm pot is between 18 to 22 cm and height above the pot is only 9 to 11 cm. Plants are usefully very long lasting under low light indoor conditions. The new variety is a *Sansevieria*, typically produced as an ornamental plant.

10 Drawing Sheets

Latin name of the genus and species: *Sansevieria trifasciata.*

Cultivar denomination: 'HANSOTI63'.

BACKGROUND OF THE INVENTION

The present invention relates to a new and distinct cultivar of *Sansevieria* plant, botanically known as *Sansevieria trifasciata* of the family Asparagaceae, hereinafter referred to by the cultivar name 'HANSOTI63'. *Sansevieria* has now been reclassified as *Dracaena* meaning this new cultivar could also be correctly referred to as *Dracaena trifasciata.*

*Sansevieria* is a monocotyledonous plant with fleshy, succulent leaves which are available in a huge range of species, varieties and cultivars as an outdoor ornamental plant (under tropical or warm temperate conditions) or as indoor plants. Both, the parental 'Hansoti41' U.S. Plant Pat. No. 36,221 and the new cultivar 'Hansoti63' belong to the group of *Sansevieria trifasciata* called "Birds Nest" or 'Hahnii' *Sansevieria* Group of very short or dwarf cultivars all ultimately derived from the original *Sansevieria trifasciata* 'Hahnii' patented in 1941 (U.S. Plant Pat. No. 470), in contrast to the medium sized "Compact *Sansevieria* Group" with *Sansevieria trifasciata* 'Futura Superba', unpatented as the typical example, and the "Tall *Sansevieria* Group" of *Sansevieria trifasciata* cultivars with tall leaves up to or even beyond 4 feet (1.25 meters) tall and *Sansevieria trifasciata* 'Laurentii', unpatented as the typical example.

The new *Sansevieria* 'HANSOTI63' was discovered and selected by Mr. Ashish Hansoti, as a single aberrant side shoot within a planting of *Sansevieria trifasciata* 'Hansoti41', a patented 'Hahnii' or "Birds Nest" type of *Sansevieria* selected and grown at this nursery at Village Asle, District Satara, Maharashtra State in Western India. Thus, it originated as a naturally occurring mutation from *Sansevieria trifasciata* cultivar 'Hansoti41' (U.S. Plant Pat. No. 36,221) in early 2021.

Asexual reproduction of the new *Sansevieria* cultivar 'Hansoti63' by vegetative cuttings was first performed around March 2022 and continued propagation and selection of true to type material was continued at Village Asle, District Satara, in Maharashtra State in Western India. After several rounds of selection of true to type shoots and discarding of off-types, it was seen that the distinctive combination of characteristics of the new cultivar reproduced true to type as long as the propagation was done through side shoots originating from the base of the parent plant (basal suckers). Thus, it can be said that the new cultivar reproduces true to type through side shoots (basal suckers) only.

BRIEF SUMMARY OF THE INVENTION

The following traits have been repeatedly observed and are determined to be unique characteristics of 'HANSOTI63', which in combination distinguish this *Sansevieria* as a new and distinct cultivar:

1. Twisted, curved leaves forming a relatively flat, somewhat open spiral-form rosette that gives a vertically compressed appearance as opposed to most other *S. trifasciata* 'Hahnii' cultivars where the leaves are more or less straight and vertically oriented. The spiral rosette is typically slightly asymmetrical when seen from top.
2. Total mature-plant width in a 9 cm pot is between 18 to 22 cm and height above the pot is only 9 to 11 cm.
3. Unlike its parent, 'Hansoti41', there is no variegation. Leaf coloration is a greyish green with typical *S. trifasciata* dark green striations
4. The plants of 'Hansoti63' thus present as a dark green spiral rosette with silvery green highlights due to the prominent *S. trifasciata* cross hatching.

'Hansoti63' has foliage phyllotaxy unlike most other Hahnii types. The new cultivar has a very unusual, vertically-flat spiral foliage arrangement, asymmetrical when seen from top, giving an overall extremely distinctive and unique appearance. It could be seen as a dark green 'Hansoti41' that has lost its variegation entirely.

Leaf width is somewhat variable and the strongest, healthiest plants have the widest leaves (this is true across all *Sansevieria trifasciata* cultivars known to the inventor) though leaves in 'Hansoti63' are relatively narrow. This variation means leaf width can be anything from 4 cm to 7 cm wide depending on season, growing conditions and plant vigour and plant age. Typically, the leaves are of medium width (5 to 6 cm when measured at the widest part of the mature leaf under good growing conditions) and 15-18 cm long, ensiform but not erect; rather, most unusually, they are held almost horizontally. Leaves have a firm, waxy texture. The blades are thick & fleshy.

The new cultivar 'Hansoti63' is a cultivar of *Sansevieria* in the group denominated as "Birds Nest" or 'Hahnii' types based on its origin and overall plant form. The new cultivar presents with 10 to 12 leaves per plant when it reaches its saleable size (about 3 months from rooted liner) but over time it can grow and accumulate many more leaves and increase in overall height.

The new cultivar is moderately drought tolerant and adapts well to conditions of bright light and heavy shade (exterior and interior). The intensity of leaf color varies with exposure to light and the contrast between Cross Hatching is most intense under higher light conditions.

The leaves have no variegation, being entirely grey-green with prominent, wide dark green striations. The typical *S. trifasciata* Cross Hatching along the width of the leaf is very distinctly seen. Younger leaves show a lighter silvery green-this becomes dull grey-green in older leaves. The basal silvery green background in recently mature leaves is near 191A. The darker green cross hatching is N189A and the same dark green color forms an indistinct thin edge to the whole leaf. With age the background silvery green turns darker and duller, approaching 137A or 137B. The backside of the leaves is similar to the top but with distinctly more silvery green seen and narrower dark green cross hatching bands and also a central narrow band of brighter green along the midrib. The silvery green at the back is near 191B; the darker green cross hatching is, as on the top, near N189A. The green band along the proximal half of the leaf along its center is near 139A.

PARENTAL COMPARISON

Plants of the new *Sansevieria* 'HANSOTI63' are similar to plants of the parental cultivar, however, 'HANSOTI63' differs in the characteristics described in Table I.

TABLE I

Comparison of Parental & the New cultivar 'Hansoti63'

| | Characteristic | Parent Cultivar 'Hansoti41' U.S. Plant Pat. No. 36,221 | New cultivar 'Hansoti63' |
|---|---|---|---|
| 1. | Leaf | 12 to 16 cm long, twisted and curved and held horizontally to form a vertically flat, spiral rosette | 15 to 18 cm long, twisted and curved along its long axis and held horizontally to form a vertically flat, spiral rosette. |
| 2. | Number of leaves | 11 to 14 leaves | 10 to 12 leaves |
| 3. | Variegation Pattern | Dark, olive-green bands on both sides with cream centres liberally streaked with grey green bands and darker green stripes. | No variegation, only prominent Cross Hatching. |
| 4. | Border variegation | 5 to 15 mm wide dark green band with almost no creamy variegation | No variegation but a thin dark green band is seen along the edge. |
| 5. | Central Variegation | 2 to 3 cm wide band of creamy yellow with streaks & bands of grey-green and stripes of dark green. *S. trifasciata* Transverse banding indistinct but seen. | No variegation, only prominent Cross Hatching typical of *S. trifasciata.* |

COMMERCIAL COMPARATOR

Plants of the new *Sansevieria* 'HANSOTI63' are similar to the commercial cultivar *Sansevieria* 'HANSOTI21', U.S. Plant Pat. No. 33,168. Plants of the new *Sansevieria* 'HANSOTI63' differ from plants of the commercial cultivar in the characteristics described in Table II.

TABLE II

Comparison of similar cultivar 'Hansoti21' and the New cultivar 'Hansoti63'

| | Characteristic | Similar Cultivar 'Hansoti21' U.S. Plant Pat. No. 33,168 | New cultivar 'Hansoti63' |
|---|---|---|---|
| 1. | Leaf | 10 to 12 cm long (Shorter) and 4-6 cm wide | 15 to 18 cm long (Longer) and 4 to 6 cm wide (Similar) |
| 2. | Number of leaves | 8 to 10 leaves (Fewer leaves) | 10 to 12 leaves (More leaves) |
| 3. | Variegation Pattern | Creamy yellow border band and green leaf centre prominently marked with typical *S. trifasciata* transverse banding. | Silvery green background color with prominent dark green cross hatching more or less dominating the leaf top surface. No variegation at all. |
| 4. | Border variegation | 3 to 15 mm creamy yellow band along both leaf borders | No border or any other variegation |
| 5. | Central Variegation | The transverse light green banding typical of *S. trifasciata* seen and prominent but no central variegation. | No variegation, only more prominent, typical *S. trifasciata* cross hatching or cross banding. |

BRIEF DESCRIPTION OF THE PHOTOGRAPHS

The accompanying photographs illustrate the overall appearance of the new *Sansevieria* cultivar 'HANSOTI63' showing the colors as true as is reasonably possible with colored reproductions of this type. Colors in the photographs may differ slightly from the color value cited in the detailed botanical description which accurately describe the color of 'HANSOTI63'.

These pictures illustrate the plant form which is the unique characteristic of 'HANSOTI63' and at the same time demonstrates comparisons with both the parent cultivar and the comparator 'Hansoti21'. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
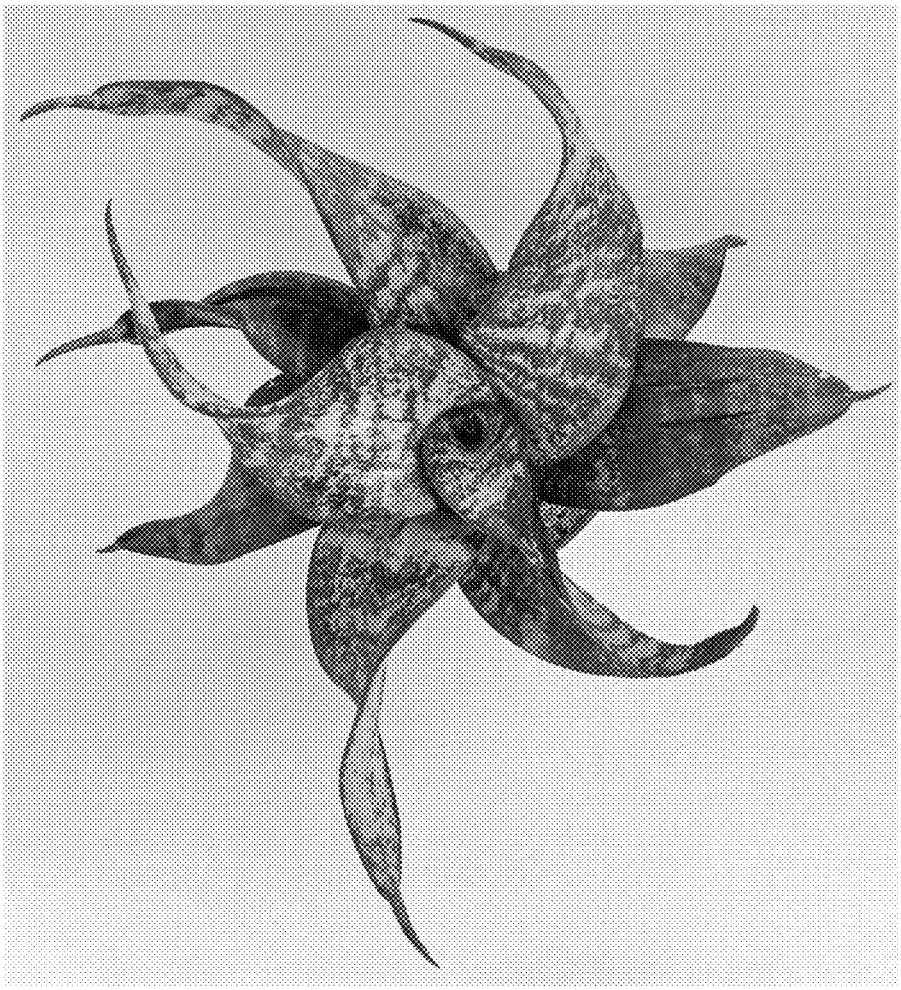
FIG. 1 illustrates a top-down view of *Sansevieria* 'HANSOTI63' in a 9 cm pot. This plant is 12 weeks old from a rooted cutting.
Figure 2:
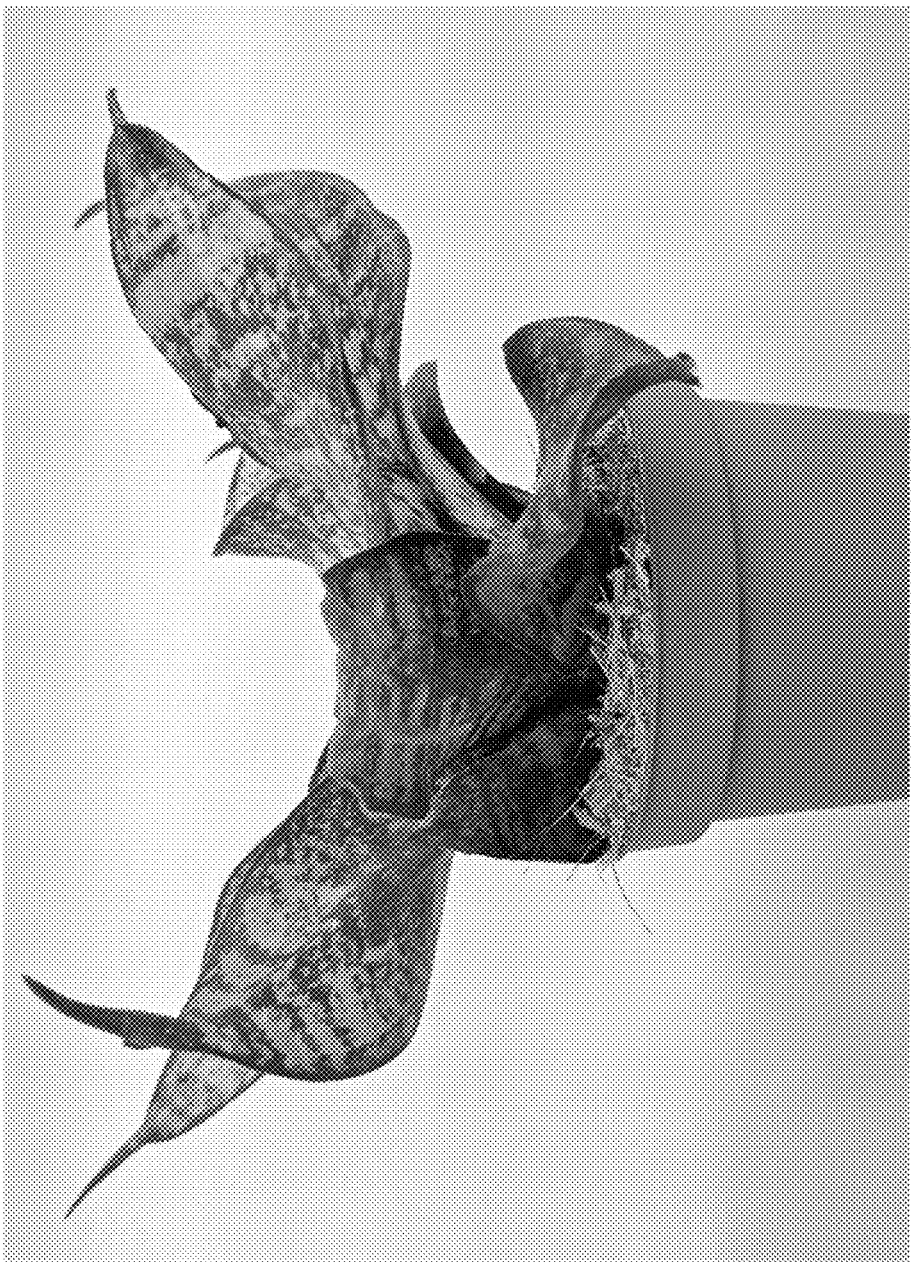
FIG. 2 illustrates the same plant as FIG. 1 from a side view.
Figure 3:
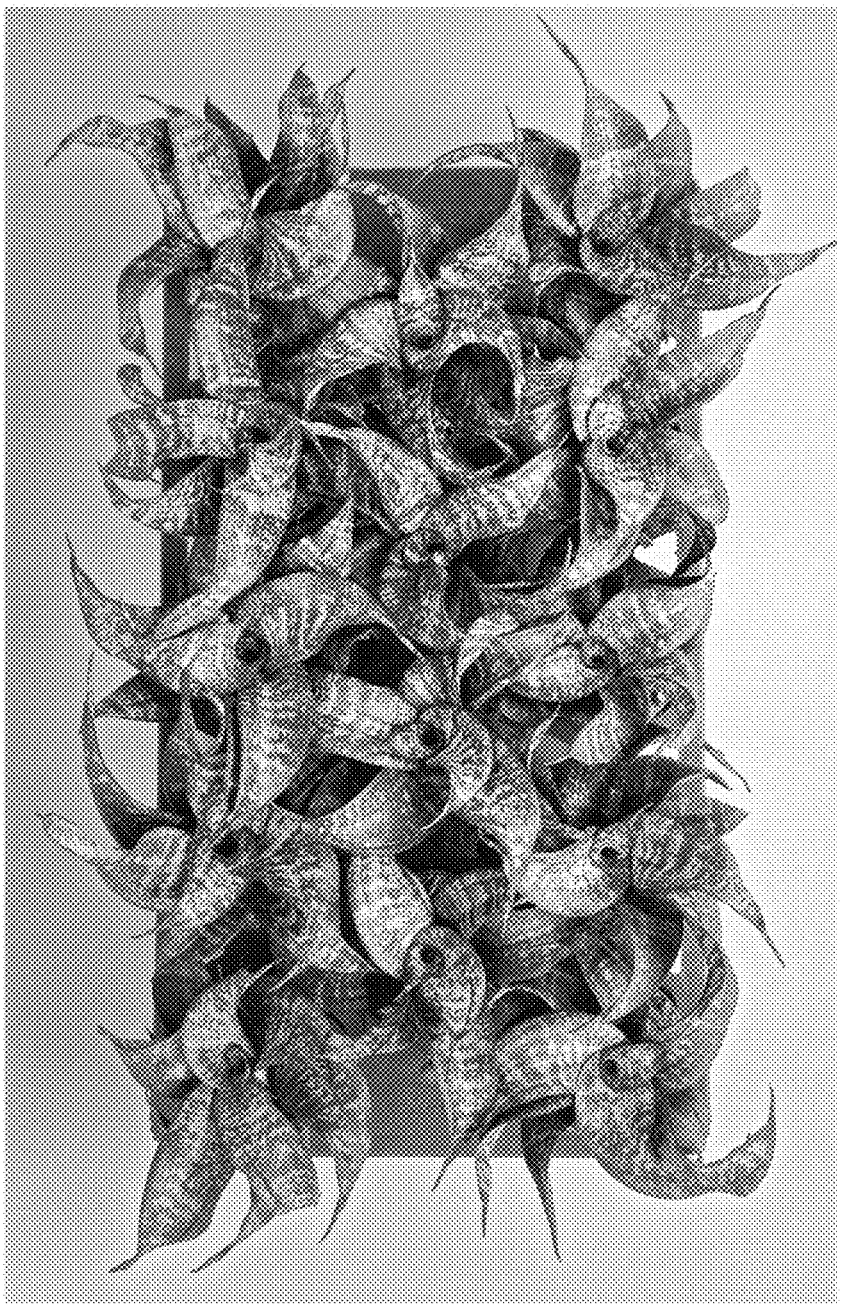

FIG. 3 shows a group of 14 'Hansoti63' plants in a tray, showing uniformity across multiple plants of this new cultivar. Plants are in 9 cm pots. The photograph was taken from a top-down view. Each plant is 12 weeks old from a rooted cutting.

Figure 4:
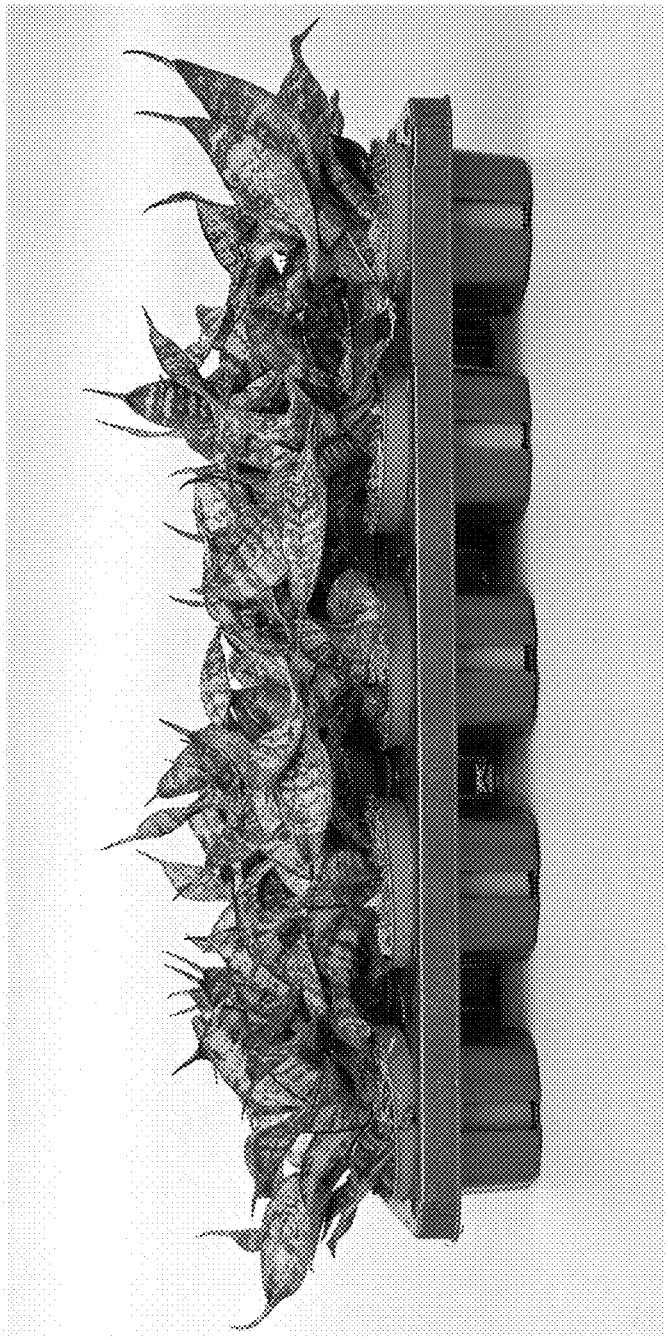

FIG. 4 is a photograph of the same plants as in FIG. 3. This photograph was taken from a side view. Each plant is 12 weeks old from a rooted cutting.

Figure 5:
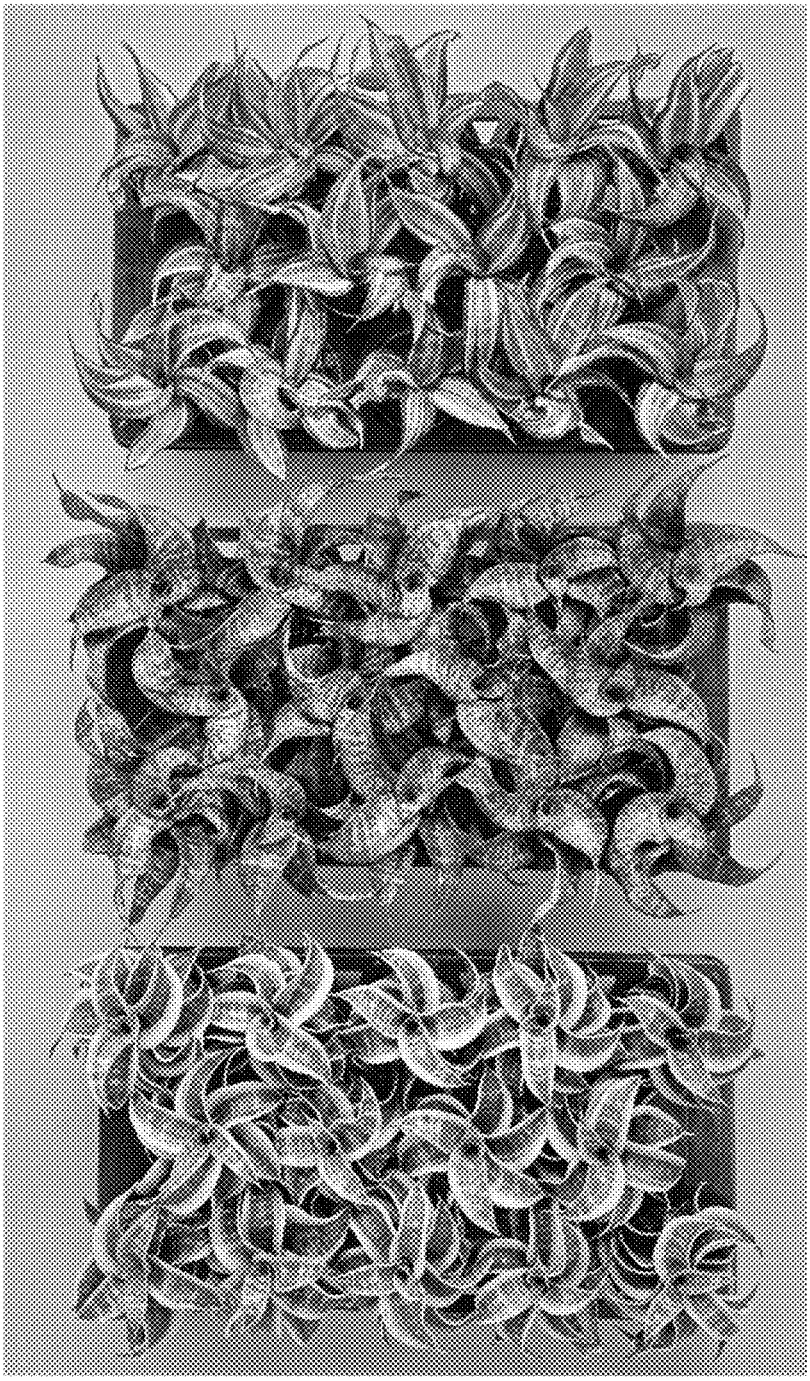

FIG. 5 is a comparison of plants of 'HANSOTI63' (center) with plants of the parent cultivar, 'Hansoti41' (right) and comparator 'Hansoti21' (left). All plants are 12 weeks old from a rooted cutting. This photograph was taken from a top-down view.

Figure 6:
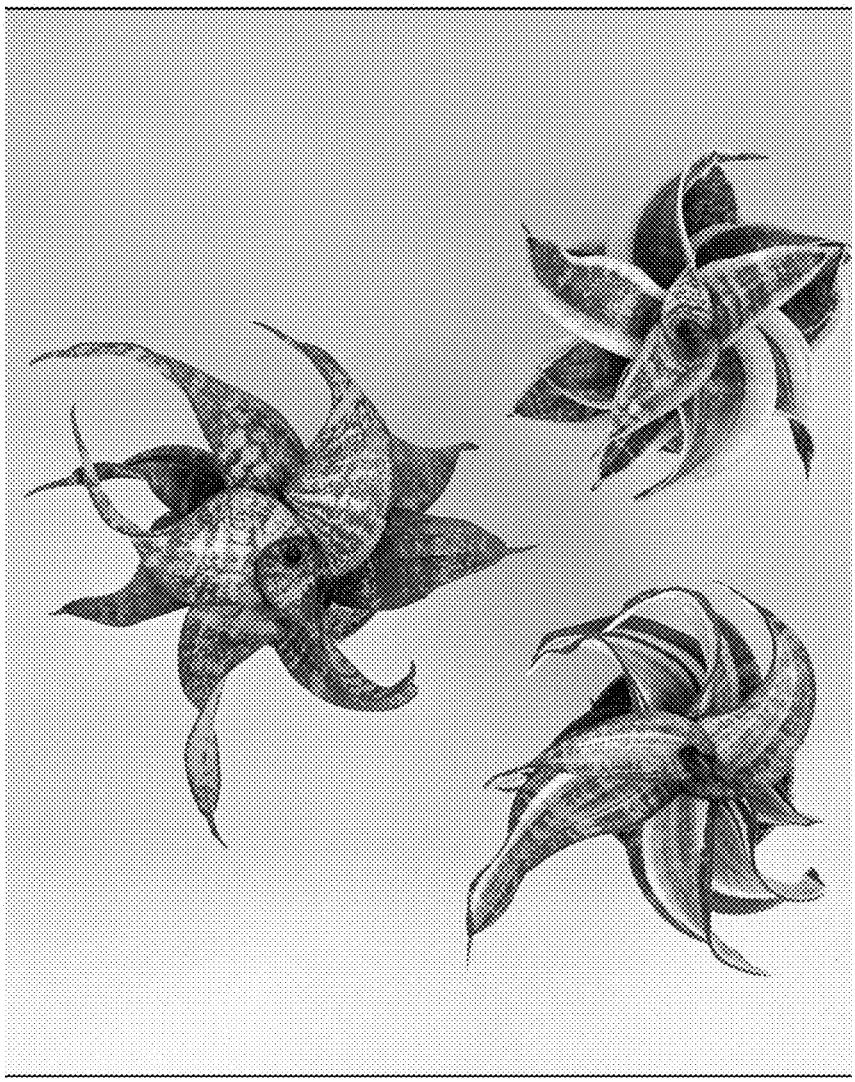

FIG. 6 is a comparison of a plant of 'HANSOTI63' (center) with the parent cultivar, 'HANSOTI41' (bottom left) and comparator 'Hansoti21' (bottom right). All plants are 3 months old from a rooted cutting. This photograph was taken from a top-down view.

Figure 7:
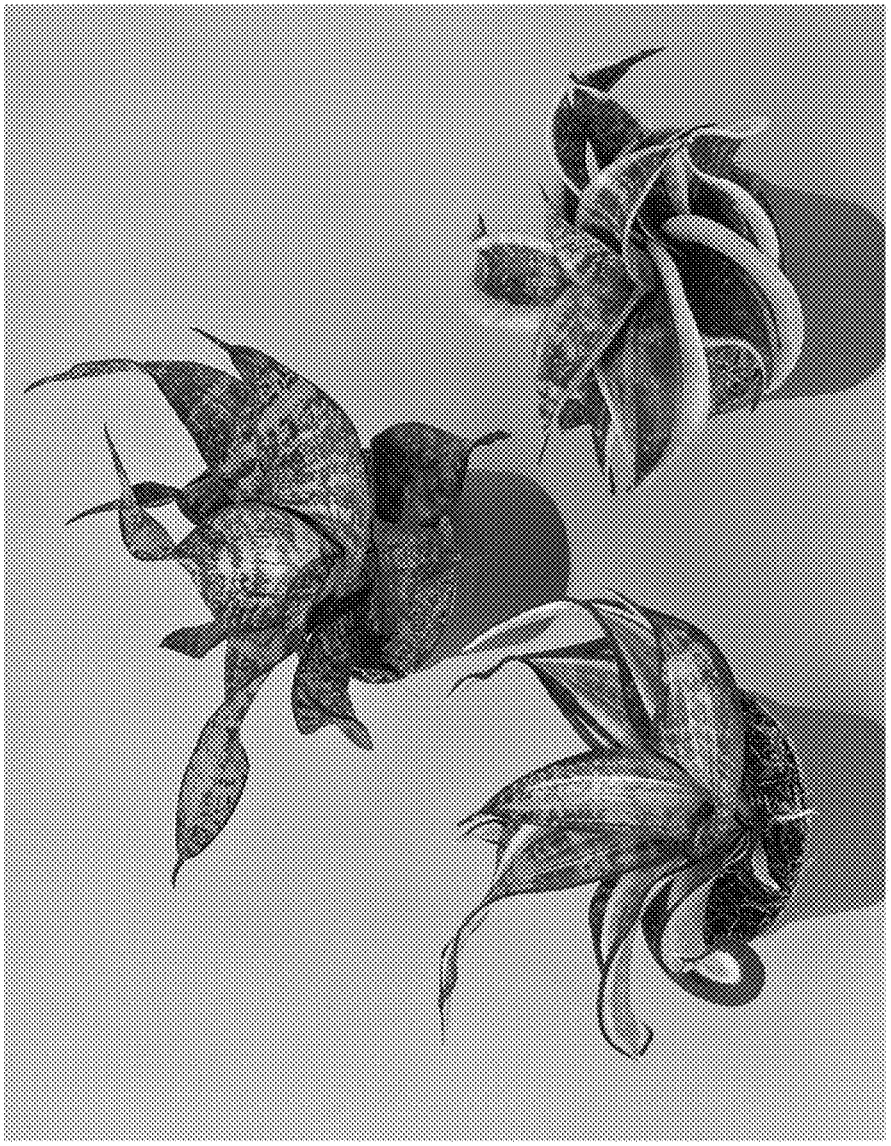

FIG. 7 is a comparison of a plant of 'HANSOTI63' (center) with the parent cultivar, 'HANSOTI41' (bottom left) and comparator 'Hansoti21' (bottom right). All plants are 3 months old from a rooted cutting. This photograph was taken from an angle of about 45°.

Figure 8:
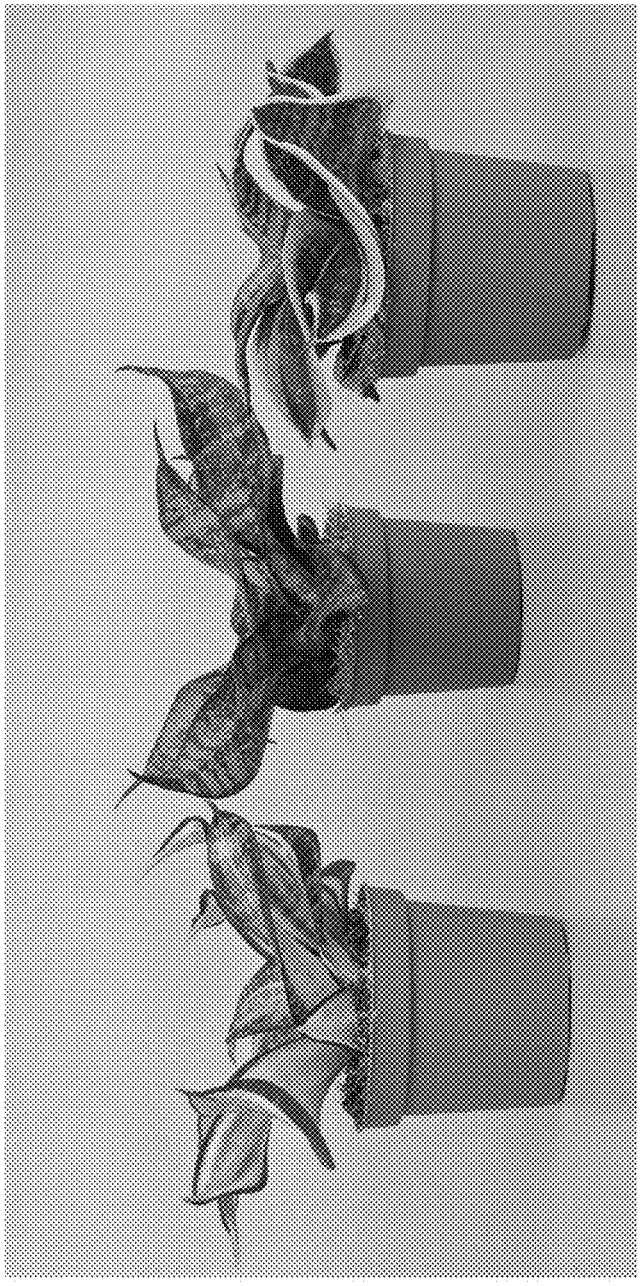

FIG. 8 is a comparison of a plant of 'HANSOTI63' (center) with the parent cultivar, 'HANSOTI41' (left) and comparator 'Hansoti21' (right). All plants are 3 months old from a rooted cutting. This photograph was taken from a side view.

Figure 9:
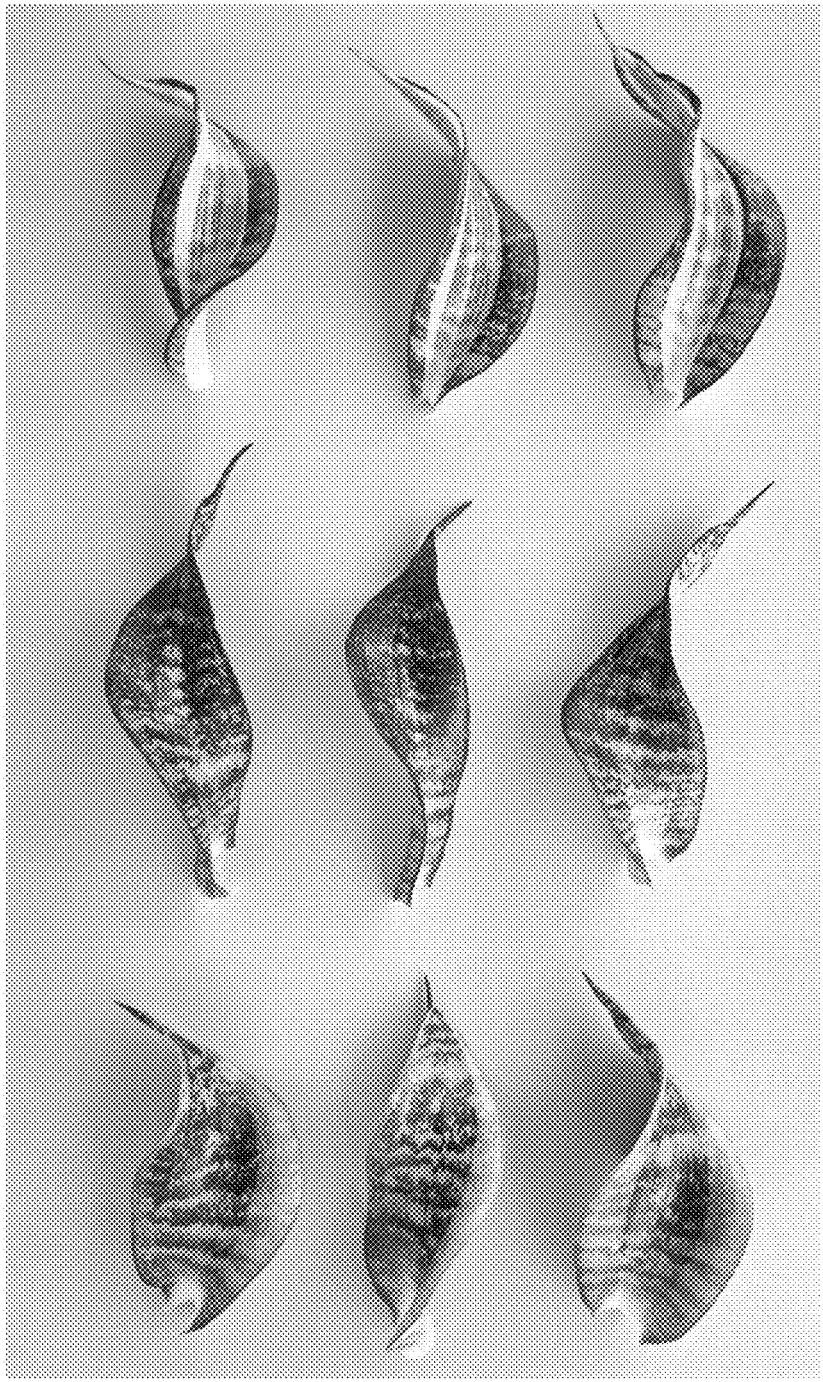

FIG. 9 is a comparison of adaxial leaf surfaces of the parental cultivar 'Hansoti41' (right), comparator 'Hansoti21' (left) and 'Hansoti63' (center).

Figure 10:
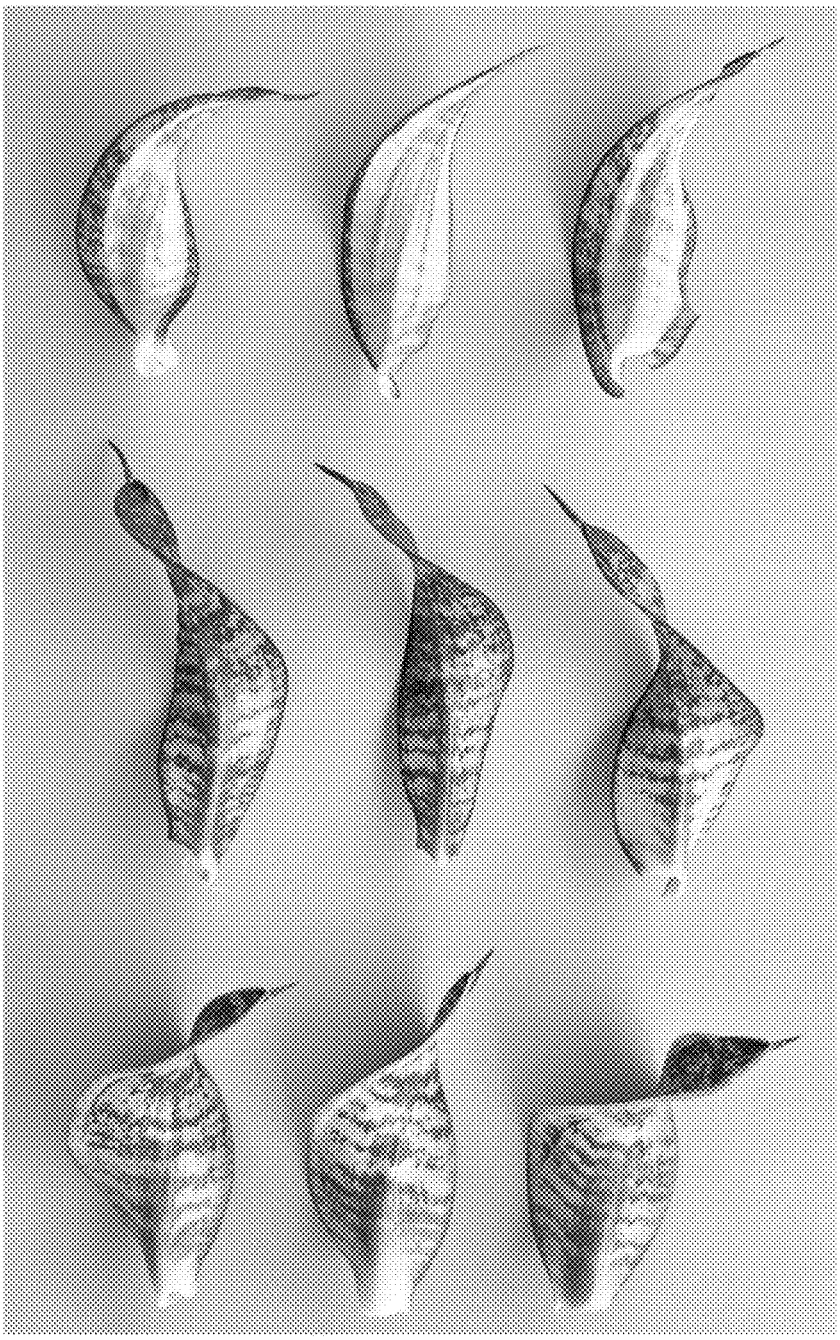

FIG. 10 is a comparison of abaxial leaf surfaces of the parental cultivar 'Hansoti41' (right), comparator 'Hansoti21' (left) and 'Hansoti63' (center).

DETAILED BOTANICAL DESCRIPTION

The new *Sansevieria* 'HANSOTI63' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI63' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11 Type 360-days release at 1 kilo/cubic meter of media, liquid fertilizer at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Color Chart (R.H.S.) 2007 ($5^{th}$ Edition), except where general colors of ordinary significance are used. It should be noted that colors in *Sansevieria* are somewhat variable depending on light levels, nutrition balance, age of plant and other factors. Plant & leaf size, width, thickness and color can vary considerably depending on light levels, feed composition and EC and pot size.

The photographs and descriptions were taken during the winter season in Asle, District Satara, Maharashtra State, India when outdoor day and temperatures were 32° C. to 38° C. and nights, usually of 25° C. to 28° C. The age of the plants described is 3-4 months in 12 cm pots.

Botanical classification: *Sansevieria trifasciata* 'HANSOTI63'.

General information:

*Parentage*.—Single aberrant side shoot within a planting of *Sansevieria trifasciata* 'Hansoti41' U.S. Plant Pat. No. 36,221.

*Optimal growth conditions*.—High adaptability to outdoor or indoor conditions.

*Light intensities*.—High adaptability to outdoor or indoor conditions but needs some shade in hot climates.

*Temperature*.—Day: 25° C. to 35° C. Night: 15° C. to 25° C.

*Temperature tolerance*.—Tolerant to a low temperature of about 6° C. and a high temperature of 38° C. and above, very heat tolerant.

*Fertilization*.—Constant feed of 100 ppm N, 20 ppm P and 100 ppm K is used along with micronutrients with occasional leaching. Media incorporation of 13:11:11 Type 360 days release at 1 kg/cubic meter of media.

*Growth regulators*.—Not necessary for growing this cultivar. Rooting hormone helps rapid and prolific rooting of offsets.

Propagation:

*Typical*.—Vegetative, by side suckers which come true to type. Does not come true from leaf cuttings.

*Rooting habit and description*.—Rhizomes elongated, fleshy, giving rise to offsets (side shoots). Offsets root easily with fibrous adventitious roots from cut end.

*Time to initiate roots*.—15 to 20 days at 25° C. to 30° C.

*Time to produce a rooted liner*.—About 45 days at 25° C. to 30° C.

*Time to produce ready* 12 *cm potted plant from liner*.—About 3 months at 25° C. to 30° C.

Plant:

*General appearance and form*.—Monocot; leaf bases arranged in a rosette around growth point.

*Height*.—About 9 to 11 cm when grown in 9 cm pots.

*Diameter*.—About 18 to 22 cm when grown when grown in a 9 cm size container.

*Rosette height* (*center*).—About 7 cm.

*Rosette diameter*.—About 18 to 22 cm.

*Growth habit*.—Upright.

*Shape*.—Inverted triangle.

*Fragrance*.—None.

*Stem*.—Modified rhizome which are fleshy with erect foliage. Texture: Smooth, waxy. Color: Greyed-Green 191A. Strength: Strong and durable.

*Internode length*.—About 1 mm.

Foliage:

*Quantity*.—About 10 to 12 in ready to sell plant in a 9 cm pot. Number slowly increases with age.

*Arrangement and attachment*.—Single, alternate; leaf bases arranged stiffly in a rosette around growth point.

*Leaf length*.—About 15 to 18 cm in mature, full-size leaf.

*Leaf width*.—About 4 to 6 cm in mature, full-size leaf.

*Overall shape of leaf*.—Lanceolate, twisted along long axis.

*Apex shape*.—Acute, triangular and aristate with soft tip.

*Base shape*.—Truncate.

*Margin*.—Entire. Sharp.

*Texture*.—Upper Surface: Smooth and waxy texture.

*Texture*.—Under Surface: Smooth and waxy texture.

*Pubescence*.—None.

*Attachment*.—Sessile.

*Color of a recently mature leaf*.—Because the leaves are held so upright, the most prominently visible surface of each leaf is, technically, the lower surface while the upper surface is mostly hidden inside the rosette.

*Upper surface*.—Silvery green basal colour near 191A with liberal amount of dark green cross hatching near N189A.

*Crossbanding*.—Seen very prominently on top surface, giving the whole leaf a dark green 139A appearance; distinct on bottom surface of leaf also but less prominent.

*Lower surface*.—Mostly as above but the silver green, near 191B is more prominent and the cross-hatching darker bands are narrower, near N189A in color; a thin dark green (139A) border along the edges of the leaf is seen. A narrow central dark green band is seen in proximal half of mature leaves and is near 139A in color.

*Venation pattern*.—Longitudinal/parallel to leaf shape. No color distinct from leaf blade.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows *Anthracnose*. Largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI63' as herein illustrated and described.

* * * * *